(12) United States Patent
Shuros

(10) Patent No.: US 7,894,906 B2
(45) Date of Patent: Feb. 22, 2011

(54) AMELIORATION OF CHRONIC PAIN BY ENDOLYMPHATIC STIMULATION

(75) Inventor: Allan C. Shuros, St. Paul, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 972 days.

(21) Appl. No.: 11/422,414

(22) Filed: Jun. 6, 2006

(65) Prior Publication Data
US 2007/0282390 A1   Dec. 6, 2007

(51) Int. Cl.
*A61N 1/34* (2006.01)

(52) U.S. Cl. .......................... 607/46; 607/45; 607/115; 607/116

(58) Field of Classification Search ................ 607/46, 607/57, 70, 48, 50, 66, 71, 74; 600/377; 128/633, 637, 630; 514/12
See application file for complete search history.

(56) References Cited

U.S. PATENT DOCUMENTS

| | | | |
|---|---|---|---|
| 3,814,080 A | 6/1974 | Norman | |
| 3,916,875 A | 11/1975 | Toch | |
| 4,792,330 A | 12/1988 | Lazarus et al. | |
| 4,957,484 A | 9/1990 | Murtfeldt | |
| 5,112,303 A | 5/1992 | Pudenz et al. | |
| 5,188,104 A | 2/1993 | Wernicke et al. | |
| 5,263,480 A | 11/1993 | Wernicke et al. | |
| 5,284,153 A | 2/1994 | Raymond et al. | |
| 5,305,745 A * | 4/1994 | Zacouto | 600/324 |
| 5,387,231 A * | 2/1995 | Sporer | 607/48 |
| 5,391,143 A | 2/1995 | Kensey | |
| 5,423,872 A | 6/1995 | Cigaina | |
| 5,655,548 A | 8/1997 | Nelson et al. | |
| 5,817,138 A * | 10/1998 | Suzuki | 607/67 |
| 5,865,744 A | 2/1999 | Lemelson | |
| 6,024,704 A | 2/2000 | Meador et al. | |
| 6,077,227 A | 6/2000 | Miesel | |
| 6,106,477 A | 8/2000 | Miesel et al. | |
| 6,129,685 A | 10/2000 | Howard, III | |
| 6,238,423 B1 * | 5/2001 | Bardy | 607/40 |
| 6,272,370 B1 | 8/2001 | Gillies et al. | |

(Continued)

FOREIGN PATENT DOCUMENTS

EP    1504778 A2    2/2005

(Continued)

OTHER PUBLICATIONS

J. Sobotta and J.P. McMurrich. Atlas of Human Anatomy, vol. III: W.B. Sauder Company, pp. 274-275.*

(Continued)

*Primary Examiner*—Carl H Layno
*Assistant Examiner*—Paula J Stice
(74) *Attorney, Agent, or Firm*—Schwegman, Lundberg & Woessner, P.A.

(57) ABSTRACT

A device and method are disclosed for treating chronic pain by delivering electrical stimulation to nervous tissue or smooth muscle fibers by means of electrodes disposed in the body's lymphatic system. An implanted pulse generator is connected to an electrode by a lead that may be intravenously introduced into the lymphatic system. The stimulation may be patient-controlled or be delivered in accordance with a programmed schedule.

10 Claims, 3 Drawing Sheets

U.S. PATENT DOCUMENTS

| | | |
|---|---|---|
| 6,292,695 B1 | 9/2001 | Webster, Jr. et al. |
| 6,321,109 B2 | 11/2001 | Ben-Haim et al. |
| 6,368,274 B1 | 4/2002 | Van Antwerp et al. |
| 6,370,417 B1 | 4/2002 | Horbaschek et al. |
| 6,475,223 B1 | 11/2002 | Werp et al. |
| 6,535,764 B2 | 3/2003 | Imran et al. |
| 6,542,776 B1 | 4/2003 | Gordon et al. |
| 6,587,719 B1 | 7/2003 | Barrett et al. |
| 6,606,523 B1 | 8/2003 | Jenkins |
| 6,609,025 B2 | 8/2003 | Barrett et al. |
| 6,611,715 B1 | 8/2003 | Boveja |
| 6,615,084 B1 | 9/2003 | Cigaina |
| 6,676,686 B2 | 1/2004 | Naganuma |
| 6,678,557 B1 | 1/2004 | Tumey |
| 6,684,104 B2 | 1/2004 | Gordon et al. |
| 6,741,882 B2 | 5/2004 | Schaffter et al. |
| 6,804,558 B2 | 10/2004 | Haller et al. |
| 6,826,428 B1 | 11/2004 | Chen et al. |
| 6,835,194 B2 | 12/2004 | Johnson et al. |
| 6,865,416 B2 | 3/2005 | Dev et al. |
| 6,879,859 B1 | 4/2005 | Boveja |
| 6,889,076 B2 | 5/2005 | Cigaina |
| 6,895,278 B1 | 5/2005 | Gordon |
| 6,918,873 B1 | 7/2005 | Millar et al. |
| 6,950,707 B2 | 9/2005 | Whitehurst |
| 7,526,337 B2 | 4/2009 | Shuros et al. |
| 7,734,341 B2 | 6/2010 | Shuros |
| 2001/0037061 A1* | 11/2001 | Eckmiller et al. ........... 600/377 |
| 2001/0041870 A1 | 11/2001 | Gillis et al. |
| 2002/0016615 A1 | 2/2002 | Dev et al. |
| 2002/0029037 A1 | 3/2002 | Kim |
| 2002/0072780 A1 | 6/2002 | Foley |
| 2002/0087192 A1 | 7/2002 | Barrett et al. |
| 2002/0123674 A1 | 9/2002 | Plicchi et al. |
| 2002/0156462 A1 | 10/2002 | Stultz |
| 2002/0188253 A1 | 12/2002 | Gordon et al. |
| 2003/0018247 A1 | 1/2003 | Gonzalez |
| 2003/0036773 A1 | 2/2003 | Whitehurst et al. |
| 2003/0055463 A1 | 3/2003 | Gordon et al. |
| 2003/0078623 A1 | 4/2003 | Weinberg et al. |
| 2003/0105506 A1 | 6/2003 | Krishnan et al. |
| 2003/0113303 A1 | 6/2003 | Schwartz |
| 2003/0114895 A1 | 6/2003 | Gordon et al. |
| 2003/0144708 A1 | 7/2003 | Starkebaum |
| 2003/0204185 A1 | 10/2003 | Sherman et al. |
| 2004/0015201 A1 | 1/2004 | Greenstein |
| 2004/0024428 A1 | 2/2004 | Barrett et al. |
| 2004/0039427 A1 | 2/2004 | Barrett et al. |
| 2004/0088022 A1 | 5/2004 | Chen |
| 2004/0102804 A1 | 5/2004 | Chin |
| 2004/0106953 A1 | 6/2004 | Yomtov et al. |
| 2004/0147976 A1 | 7/2004 | Gordon et al. |
| 2004/0158297 A1 | 8/2004 | Gonzalez |
| 2004/0162595 A1 | 8/2004 | Foley |
| 2004/0172102 A1* | 9/2004 | Leysieffer ........... 607/57 |
| 2004/0193229 A1 | 9/2004 | Starkebaum et al. |
| 2004/0210118 A1 | 10/2004 | Letort |
| 2004/0230255 A1 | 11/2004 | Dobak, III |
| 2005/0033376 A1 | 2/2005 | Whitehurst |
| 2005/0043675 A1 | 2/2005 | Pastore et al. |
| 2005/0043894 A1 | 2/2005 | Fernandez |
| 2005/0049472 A1 | 3/2005 | Manda et al. |
| 2005/0065575 A1 | 3/2005 | Dobak |
| 2005/0070974 A1 | 3/2005 | Knudson et al. |
| 2005/0075678 A1 | 4/2005 | Faul |
| 2005/0075701 A1 | 4/2005 | Shafer |
| 2005/0075702 A1 | 4/2005 | Shafer |
| 2005/0080346 A1 | 4/2005 | Gianchandani et al. |
| 2005/0080462 A1 | 4/2005 | Jenkins et al. |
| 2005/0090873 A1 | 4/2005 | Imran |
| 2005/0143765 A1 | 6/2005 | Bachmann et al. |
| 2005/0143787 A1 | 6/2005 | Boveja et al. |
| 2005/0149014 A1 | 7/2005 | Hauck et al. |
| 2005/0149141 A1 | 7/2005 | Starkebaum |
| 2005/0149142 A1 | 7/2005 | Starkebaum |
| 2005/0149157 A1 | 7/2005 | Hunter et al. |
| 2005/0187584 A1 | 8/2005 | Denker et al. |
| 2005/0222637 A1 | 10/2005 | Chen |
| 2005/0222638 A1 | 10/2005 | Foley et al. |
| 2005/0240239 A1 | 10/2005 | Boveja et al. |
| 2005/0240243 A1 | 10/2005 | Barolat et al. |
| 2005/0246006 A1* | 11/2005 | Daniels .................. 607/117 |
| 2005/0267440 A1 | 12/2005 | Herman et al. |
| 2005/0273060 A1 | 12/2005 | Levy et al. |
| 2005/0288729 A1* | 12/2005 | Libbus et al. ............. 607/42 |
| 2005/0288730 A1 | 12/2005 | Deem et al. |
| 2006/0020333 A1 | 1/2006 | Lashinski et al. |
| 2006/0030837 A1 | 2/2006 | McKenna et al. |
| 2006/0074453 A1 | 4/2006 | Kieval et al. |
| 2006/0247601 A1 | 11/2006 | Ellin et al. |
| 2007/0021731 A1 | 1/2007 | Garibaldi et al. |
| 2007/0027460 A1 | 2/2007 | Case et al. |
| 2007/0244520 A1 | 10/2007 | Ferren et al. |
| 2007/0255340 A1* | 11/2007 | Giftakis et al. ............. 607/46 |
| 2007/0282376 A1 | 12/2007 | Shuros |
| 2007/0282382 A1 | 12/2007 | Shuros et al. |
| 2007/0282386 A1 | 12/2007 | Shuros |
| 2008/0009719 A1 | 1/2008 | Shuros et al. |
| 2008/0058887 A1 | 3/2008 | Griffin et al. |
| 2008/0086185 A1 | 4/2008 | Amurthur et al. |
| 2008/0097412 A1 | 4/2008 | Shuros et al. |
| 2008/0260861 A1 | 10/2008 | Hagendoorn et al. |
| 2008/0294228 A1 | 11/2008 | Brooke et al. |
| 2009/0228059 A1 | 9/2009 | Shuros |
| 2010/0042170 A1 | 2/2010 | Shuros et al. |

FOREIGN PATENT DOCUMENTS

| | | |
|---|---|---|
| SU | 1074527 A * | 2/1984 |
| WO | WO-93/14694 A1 | 8/1993 |
| WO | WO-9314694 A1 | 8/1993 |
| WO | WO-03/098177 A2 | 11/2003 |
| WO | WO-03098177 A2 | 11/2003 |
| WO | WO-2004/006795 A1 | 1/2004 |
| WO | WO-2004006795 A1 | 1/2004 |
| WO | WO-2004/032791 A2 | 4/2004 |
| WO | WO-2005/089863 A1 | 9/2005 |
| WO | WO-2007/067690 A2 | 6/2007 |
| WO | WO-2007/146489 A2 | 12/2007 |
| WO | WO-2007/146493 A1 | 12/2007 |
| WO | WO-2007/146517 A2 | 12/2007 |
| WO | WO-2008/030344 A2 | 3/2008 |

OTHER PUBLICATIONS

Yimtae et al., "Connection Between the Inner Ear adn the Lymphatic System", Laryngoscope 111: Sep. 2001.*

U.S. Appl. No. 11/422,417, Restriction Requirement mailed Jul. 25, 2007, 5 pgs.

"U.S. Appl. No. 11/422,417, Non-Final Office Action mailed Sep. 25, 2007", 7 pgs.

"U.S. Appl. No. 11/422,417, Non-Final Office Action mailed Apr. 21, 2008", 7 pgs.

"U.S. Appl. No. 11/422,417, Notice of Allowance mailed Dec. 12, 2008", 4 pgs.

"U.S. Appl. No. 11/422,417, Response filed Aug. 21, 2008 to Non Final Office Action mailed Apr. 21, 2008", 6 pgs.

"U.S. Appl. No. 11/422,417, Response filed Aug. 27, 2007 to Restriction Requirement mailed Jul. 25, 2007", 4 pgs.

"U.S. Appl. No. 11/422,417, Restriction Requirement mailed Jul. 25, 2007", 5 pgs.

"U.S. Appl. No. 11/422,417, Response filed Jan. 25, 2008 to Non-Final Office Action mailed Sep. 25, 2007", 7 pgs.

"U.S. Appl. No. 11/422,418, Non-Final Office Action mailed Sep. 15, 2008", 11 pgs.

"U.S. Appl. No. 11/422,418, Response filed Dec. 15, 2008 to Non-Final Office Action mailed Sep. 15, 2008", 15 pgs.

"U.S. Appl. No. 11/422,418, Restriction Requirement mailed Mar. 25, 2009", 7 pgs.

"U.S. Appl. No. 11/422,418, Response filed Apr. 27, 2009 to Restriction Requirement mailed Mar. 25, 2009", 6 pgs.

"U.S. Appl. No. 11/422,421, Non-Final Office Action mailed Dec. 10, 2008", 16 pgs.

"U.S. Appl. No. 11/422,421, Response filed Apr. 9, 2009 to Non Final Office Action mailed Dec. 10, 2008", 12 pgs.

"U.S. Appl. No. 11/422,423, Response filed Feb. 9, 2009 to Non-Final Office Action mailed Oct. 8, 2008", 8 pgs.

"U.S. Appl. No. 11/422,423, Non-Final Office Action mailed Jan. 10, 2008", 10 pgs.

"U.S. Appl. No. 11/422,423, Non-Final Office Action mailed Oct. 8, 2008", 9 pgs.

"U.S. Appl. No. 11/422,423, Response filed May 12, 2008 to Non-Final Office Action mailed Jan. 10, 2008", 12 pgs.

"PCT Application No. PCT/US2007/068617, International Search Report mailed Mar. 10, 2008", 4 pgs.

"PCT Application No. PCT/US2007/068617, Written Opinion mailed Mar. 10, 2008", 8 pgs.

"Physician's Manual—VNS Therapy tm Lead Model 302", © 2003, 2004, 2005 Cyberonics, Inc., Houston, TX, (Jul. 2005), 35 pgs.

Amurthur, B., et al., "Distributed Neuromodulation System for Treatment of Cardiovascular Disease", U.S. Appl. No. 11/539,301, filed Oct. 6, 2006, 19 pgs.

Issa, Z. F., et al., "Thoracic spinal cord stimulation reduces the risk of ischemic ventricular arrhythmias in a postinfarction heart failure canine model", *Circulation*, 111(24), (Jun. 21, 2005), 3217-3220.

Knott, E. M., et al., "Increased lymphatic flow in the thoracic duct during manipulative intervention", *J Am Osteopath Assoc.*, 105(10), (Oct. 2005), 447-456.

Lei, Y., et al., "Effects and Mechanisms of Implantable Gastric Stimulation on Gastric Distention in Conscious Dogs", *Obesity Surgery*, 15(4), (Apr. 2005), 528-533.

Pulley, M. S., et al., "Intravenous, intralesional and endolymphatic administration of lymphokines in human cancer.", *Lymphokine Res.*, 5 Suppl 1, (1986), S157-S163.

Shuros, A. C, "Amelioration of Chronic Pain by Endolymphatic Stimulation", U.S. Appl. No. 11/422,414, filed Jun. 6, 2006, 15 pgs.

Shuros, A. C, "Method and Apparatus for Gastrointestinal Stimulation Via The Lymphatic System", U.S. Appl. No. 11/422,418, filed Jun. 6, 2006, 35 pgs.

Shuros, A. C, et al., "Method and Apparatus for Introducing Endolymphatic Instrumentation", U.S. Appl. No. 11/422,423, filed Jun. 6, 2006, 23 pgs.

Shuros, A. C, et al., "Method and Apparatus for Neural Stimulation Via The Lymphatic System", U.S. Appl. No. 11/422,421, filed Jun. 6, 2006, 35 pgs.

Shuros, A. C, et al., "Method and Device for Lymphatic System Monitoring", U.S. Appl. No. 11/422,417, filed Jun. 6, 2006, 15 pgs.

"European Application No. 07797400.4, Office Action Mailed Apr. 21, 2009", 3 pgs.

"European Application Serial No. 07782375.5 office action mailed Aug. 10, 2009", 4 pgs.

"International Application No. PCT/US2007/018631, International Search Report mailed Mar. 25, 2008", 4 pgs.

"International Application No. PCT/US2007/018631, Written Opinion mailed Mar. 25, 2008", 7 pgs.

"International Application Serial No. PCT/US2007/06178, International Search Report mailed Oct. 31, 2007", 5 pgs.

"International Application Serial No. PCT/US2007/06178, Written Opinion mailed Oct. 31, 2007", 8 pgs.

"U.S. Appl. No. 11/422,418, Notice of Allowance mailed Jan. 28, 2010", 8 pgs.

"U.S. Appl. No. 11/422,421, Advisory Action mailed Sep. 28, 2009", 5 pgs.

"U.S. Appl. No. 11/422,423, Final Office Action mailed Apr. 9, 2010", 12 pgs.

"U.S. Appl. No. 11/469,793, Non-Final Office Action mailed Mar. 12, 2010", 6 pgs.

"U.S. Appl. No. 11/752,377, Response filed Feb. 25, 2010 to Non Final Office Action mailed Nov. 27, 2009", 5 pgs.

"European Application No. 07797264.1, Office Action Mailed Jan. 20, 2010", 3 pgs.

"European Application No. 07797400.4, Response filed Oct. 12, 2009 to Communication mailed Apr. 21, 2009", 10 pgs.

"Japanese Application Serial No. 2009-514448, Amended Claims filed Feb. 6, 2009", (w/ English Translation of Claims), 9 pgs.

"U.S. Appl. No. 11/422,423 Non-Final Office Action mailed Jul. 21, 2010", 13 pgs.

"U.S. Appl. No. 11/422,423, Response filed Jul. 8, 2010 to Final Office Action mailed Apr. 9, 2010", 9 pgs.

"U.S. Appl. No. 11/469,793, Response filed Jul. 12, 2010 to Non Final Office Action mailed Mar. 12, 2010", 10 pgs.

"U.S. Appl. No. 11/752,377, Final Office Action mailed May 26, 2010", 9 pgs.

* cited by examiner

AMELIORATION OF CHRONIC PAIN BY ENDOLYMPHATIC STIMULATION

RELATED APPLICATIONS

This application is related to application Ser. Nos. 11/422,423, 11/422,417, now issued as U.S. Patent 7,526,337, 11/422,418, and 11/422,421, all filed Jun. 6, 2006 and are hereby incorporated by reference.

FIELD OF THE INVENTION

This invention pertains to methods and systems for treating disease with implantable devices.

BACKGROUND

Treating chronic pain is an important task of modern medicine. Chronic pain is a major public health problem in this country and is the cause of much physical and emotional disability. Pain may be roughly classified as being either acute or chronic. Acute pain, such as occurs after surgery or trauma, comes on suddenly and lasts for a limited time. Acute pain is a direct response to disease or injury to tissue, and typically subsides when the disease or injury is adequately treated. Chronic pain, on the other hand, is pain that persists for a long period of time, sometimes even after a known precipitating cause no longer exists. Common types of chronic pain include back pain, headaches, arthritis, cancer pain, and neuropathic pain resulting from injury to nerves.

Treating chronic pain may involve a number of different therapies such as physical rehabilitation, psychological counseling, and medications. Electrical stimulation of nervous tissue has also been found to be effective in treating certain kinds of chronic pain. Prior methods of delivering such neural electrical stimulation to relieve pain have utilized electrodes placed on the skin surface to stimulate underlying nervous tissue. Delivering neural electrical stimulation transcutaneously in this fashion, however, can only stimulate nervous tissue located at a relatively shallow depth beneath the skin surface.

SUMMARY

A device and method are disclosed for treating chronic pain by delivering electrical stimulation to nervous tissue or the smooth muscle of lymphatic vessels by means of electrodes disposed in the body's lymphatic system. An implanted pulse generator is connected to an electrode by a lead that may be intravenously introduced into the lymphatic system. The stimulation may be patient-controlled or may be delivered in accordance with a programmed schedule.

DETAILED DESCRIPTION

This disclosure relates to a device and method for delivering electrical stimulation in order to ameliorate chronic pain. In one embodiment, an electrical stimulation device is implanted in a manner similar to that of a cardiac pacemaker and has one or more leads that deliver electrical stimulation to locations accessible through the body's lymphatic vessels.

The lymphatic vessels are part of the body's circulatory system and serve as a pathway by which fluids can flow from the interstitial spaces into blood. Lymphatic vessels also communicate with lymph nodes and facilitate the body's immune function by transporting foreign antigens to the lymph nodes from the interstitial spaces. Lymphatic vessels generally run alongside nerves as they course through the body, and lymph nodes and other parts of the lymphatic system are often located near nerve endings and pain receptors. This makes the lymphatic system a convenient conduit for routing a lead from an implantable pulse generator to an electrode in order to deliver neural electrical stimulation to internal body locations. Delivering neural electrical stimulation in this manner may be used to treat pain arising from nervous tissue located near lymphatic vessels such nervous tissue near lymph nodes, the spine, or internal organs. Chronic pain may also be due to swelling of lymphatic vessels and nodes. Swelling or edema of these lymph structures causes pressure on nerve endings eliciting a pain sensation. The system may also be used to electrically stimulate the smooth muscle of the lymphatic vessels, causing the vessels to contract and empty the lymph fluid in order to reduce edema.

Figure 1:
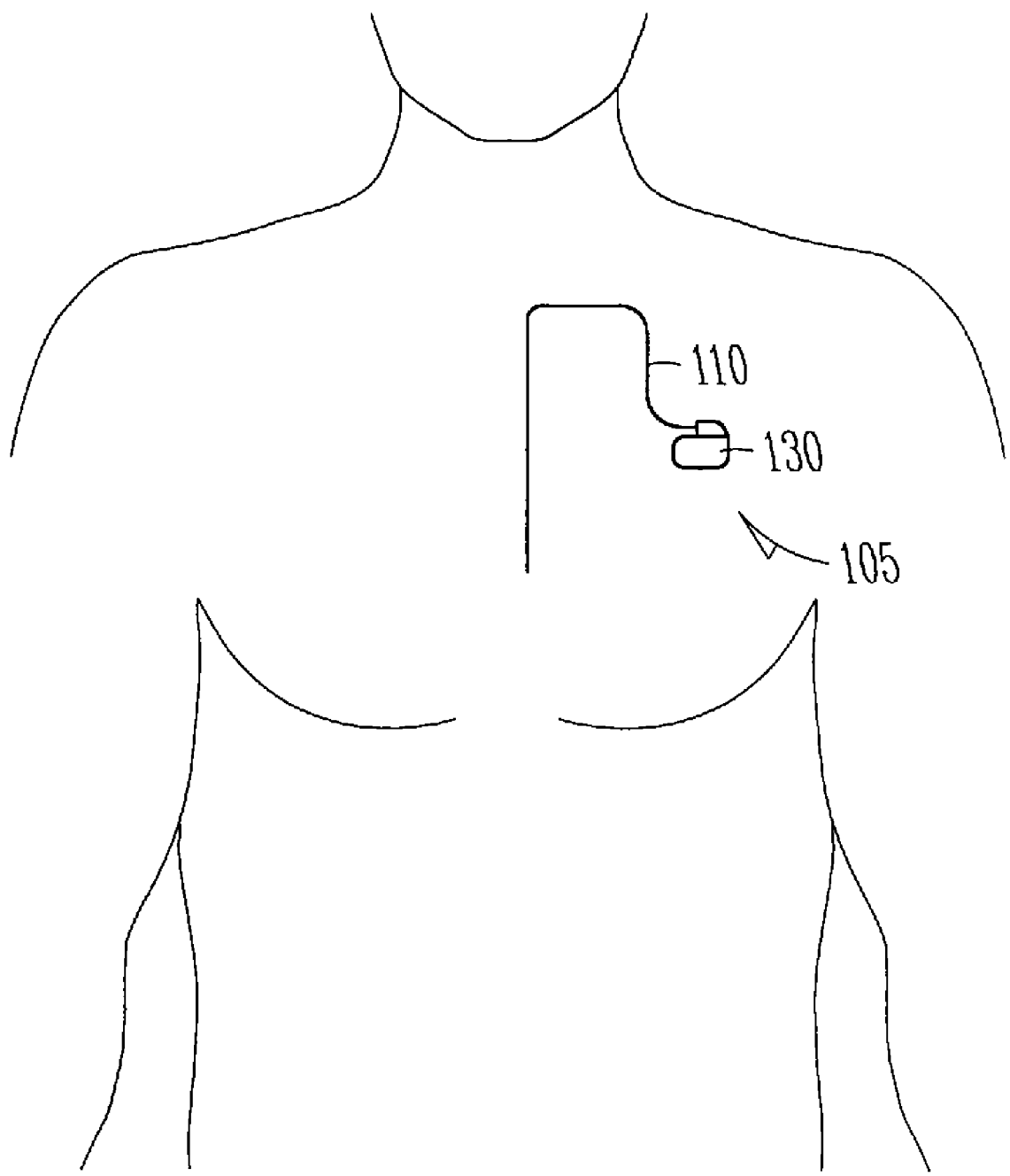
FIG. 1 illustrates the physical placement of an implanted pulse generator and stimulation lead.

FIG. 1 shows an exemplary physical placement of an implantable pulse generator as described herein. In one embodiment, an implantable pulse-generator (PG) 105 is placed subcutaneously on the patient's chest or abdomen, similar to a standard cardiac PG. The PG is connected to one or more leads 110, each having a distal member that incorporates an electrode. The lead is positioned within the lymphatic system using a venous approach which involves initial entry into the venous blood system. In the embodiment depicted in FIG. 1, the lead 110 passes subcutaneously from the device housing 130 to a point of venous access in the upper chest or neck such as the subclavian vein. The lead is then guided into the thoracic duct ostium using fluoroscopy techniques and positioned near selected areas of chronic pain within the lymphatic system. The electrode incorporated into the lead is thus positioned near nervous tissue responsible for the patient's chronic pain or near areas of edema in order to enable delivery of electrical stimulation to smooth muscle fibers of the lymphatic vessel wall and elicit activation and contraction of those muscle fibers.

Figure 2:
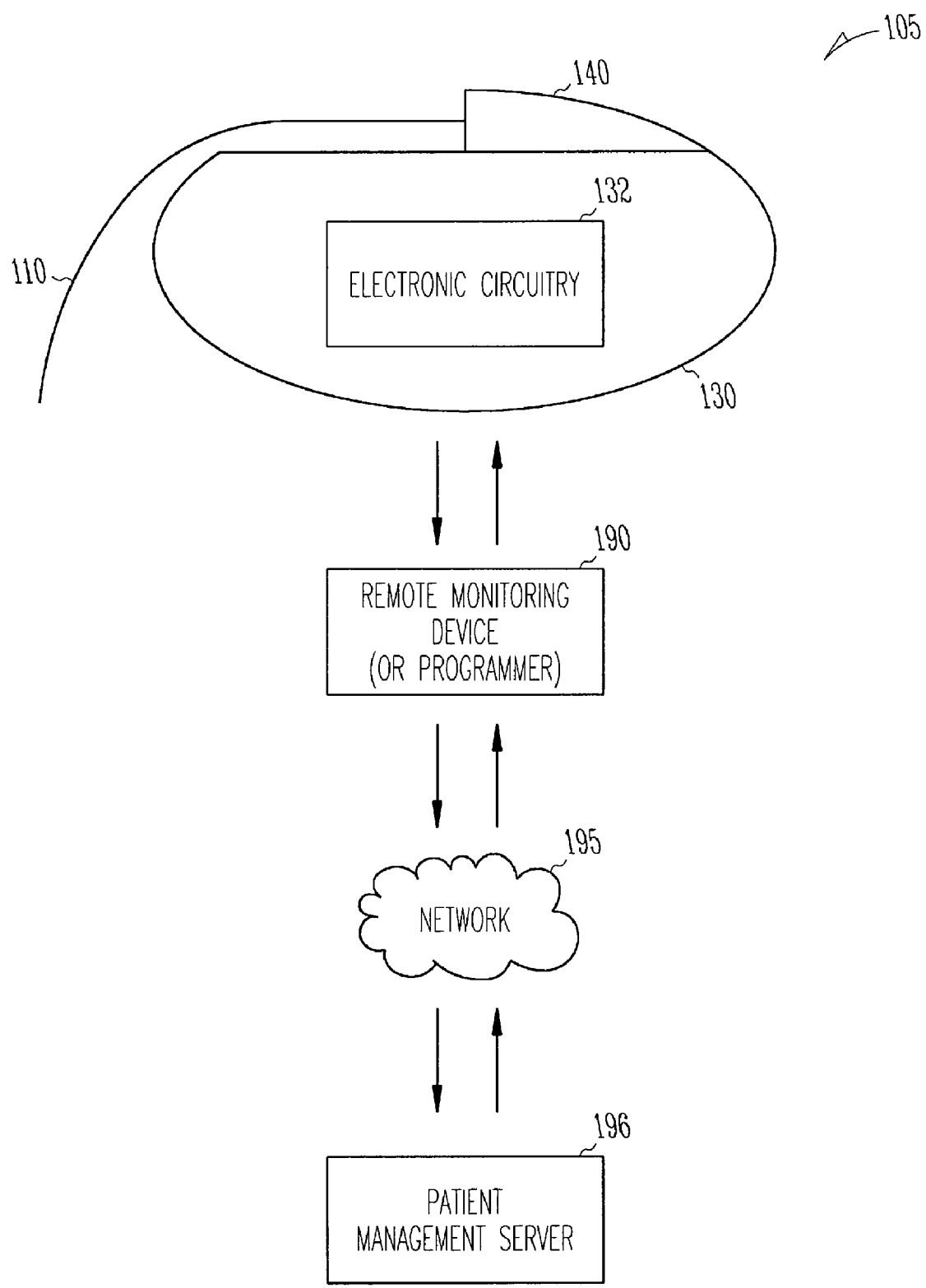
FIG. 2 illustrates the components of an exemplary system for delivering electrical stimulation through the lymphatic system to treat pain.

FIG. 2 shows an exemplary system for delivering electrical stimulation. The pulse generator 105 includes a hermetically sealed housing 130 that is placed subcutaneously or submuscularly in a patient's chest or other convenient location as noted above. The housing 130 may be formed from a conductive metal, such as titanium, and may serve as an electrode for delivering electrical stimulation with a unipolar lead. A header 140, which may be formed of an insulating material, is mounted on the housing 130 for receiving the leads 110 which are electrically connected to the pulse generation circuitry. Contained within the housing 130 is the electronic circuitry 132 for providing the functionality to the device as described herein and may include a power supply, pulse generation circuitry, and a programmable electronic controller for controlling the delivery of electrical stimulation by the pulse generation circuitry.

Figure 3:
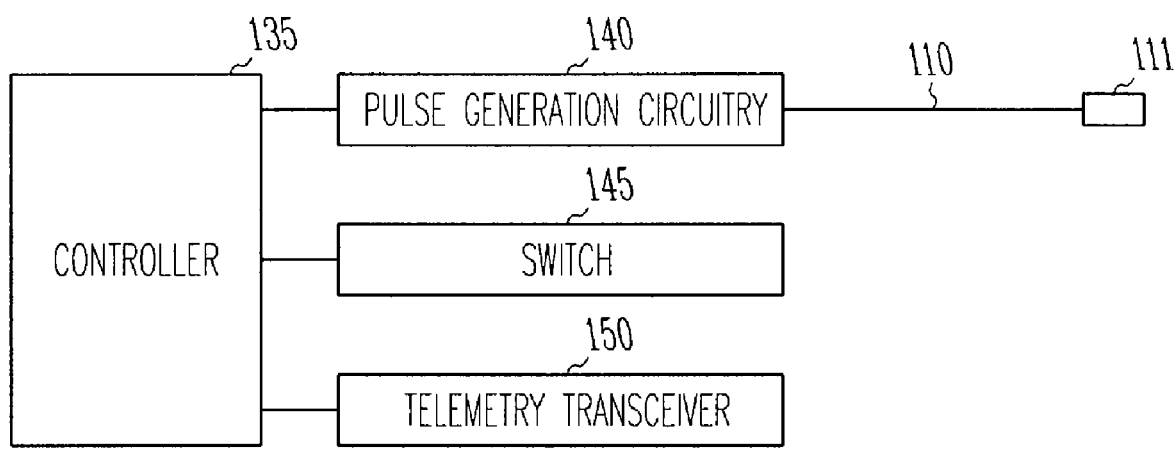
FIG. 3 illustrates a block diagram of the components of an exemplary pulse generator.

FIG. 3 illustrates exemplary components of the electronic circuitry 132 as depicted in FIG. 2. A controller 135 is provided which may be made up of discrete circuit elements but is preferably a processing element such as a microprocessor together with associated memory for program and data storage which may be programmed to perform algorithms for delivering therapy. (As the terms are used herein, "circuitry" and "controller" may refer either to a programmed processor or to dedicated hardware components configured to perform a particular task.) The controller 135 is interfaced to pulse generation circuitry 140 in order to control the delivery of electrical stimulation by the pulse generator. Pulse generation circuitry 140 is electrically connected to a lead 110 that is adapted for disposition in a patient's lymphatic system. In one embodiment, the lead 110 is a bipolar lead having at least two electrodes 111, wherein a voltage generated by the pulse generation circuitry is imposed between two electrodes of the bipolar lead. In another embodiment, the attached lead 110 is a unipolar lead such that a voltage generated by the pulse generator is imposed between the electrode of the unipolar lead and the conductive housing. The electrical stimulation may be delivered in different forms, such as a DC pulse, a biphasic pulse, a multi-phasic pulse, or a pulse train at a selected frequency for a selected duration. In the embodiment illustrated in FIG. 3, a manually operated switch 145 is interfaced to the controller in order to allow the patient to initiate delivery of pain relieving electrical stimulation as needed. The switch 145 may be, for example, a tactilely actuated switch mounted on the housing of the pulse generator so as to be accessible by the patient after implantation or may be a magnetically actuated switch so that the switch is operated when a magnet is placed in proximity to the pulse generator.

Also interfaced to the controller in FIG. 3 is a telemetry transceiver 150 capable of communicating with an external programmer or a remote monitoring device 190 as illustrated in FIG. 2. An external programmer wirelessly communicates with the device 105 and enables a clinician to receive data and modify the programming of the controller. A remote monitoring device similarly communicates with the device 105 and is further interfaced to a network 195 (e.g., an internet connection) for communicating with a patient management server 196 that allows clinical personnel at remote locations to receive data from the remote monitoring device as well as issue commands. In one embodiment, the delivery of pain relieving electrical stimulation is initiated by a command issued to the pulse generator from an external device. In another embodiment, the controller is programmed via telemetry to deliver electrical stimulation in accordance with a defined schedule. The controller may also be programmed to maintain a record of manually operated switch operations over a specified period of time and may be further programmed to transmit an alarm message (e.g., to a patient management server) via the telemetry transceiver if the number of switch operations exceeds a specified limit value. The controller could also be programmed to limit the number of times that the patient is able to actuate the manually operated switch over some defined period of time.

In order to implant a lead incorporating a stimulation electrode(s) into a selected location within lymphatic vessel, the lymphatic system may be visualized using lymphangiography. In this technique, dye is injected into the subcutaneous tissue of an extremity such as the foot, or other peripheral lymph vessel, and the lymphatic system drains the dye making the lymphatic vessels visible. A lymphatic vessel is cannulated, and radiopaque contrast is injected to illuminate major lymph vessels including the thoracic duct and its ostium into the subclavian vein. A catheter or the lead may then be guided into the thoracic duct ostium via the venous system using fluoroscopy techniques and positioned at a selected location within the lymphatic system. Initial cannulation of the lymph ostium with a guide wire or catheter may be achieved through the left or right subclavian vein, the left jugular veins, the epigastric/mammary veins or the femoral veins. In order to facilitate navigation through the lymphatic vessels and position the stimulation electrode at a selected anatomical location, an overlapping technique may be employed whereby fluoroscopic images produced by the injected dye are used in conjunction with anatomical images of the patient produced by other modalities such as conventional x-ray, CAT scans, MRI scans, or ultrasonic scans. The fluoroscopic image may be overlaid with the anatomical image and the lead then guided to the selected location.

To implant the lead, a catheter or the lead by itself may be introduced into the venous system and from there into the thoracic duct ostium using conventional over-the-wire techniques that employ a guide wire. The guide wire is manually or mechanically pushed and manipulated to guide its travel and upon which catheters and/or leads may be advanced. A stereotaxis technique in which external magnets or other means are used to guide the catheter may also be used to improve maneuverability and precision as well as provide increased safety. An example of this technique is described in U.S. Pat. No. 6,475,223, hereby incorporated by reference. Once the catheter or lead is in the lymphatic system, it must also traverse valves in the lymphatic vessels whose function is to allow flow of lymphatic fluid in only one direction to the thoracic duct. In the case where a catheter is employed, as the catheter is guided through a vessel to one of these valves, the catheter may incorporate a vacuum system to open the valves. When the vacuum system is actuated, it draws negative pressure to create a pressure gradient that opens the valve. An alternative technique for opening lymphatic valves involves using a catheter incorporating a compliant balloon on its distal tip. When the catheter reaches a lymphatic valve, the balloon is inflated to mechanically dilate the vessel which opens the valve and allows a wire or the catheter to pass through. In still another technique, the catheter incorporated an electrode at its tip (which may or may not be the stimulation electrode intended to be left in the lymphatic vessel) that is used to cause smooth muscle contraction of the lymphatic vessel. Such smooth muscle contraction can create a pressure gradient that opens the valve and allows the catheter to advance past the valve.

Although the invention has been described in conjunction with the foregoing specific embodiments, many alternatives, variations, and modifications will be apparent to those of ordinary skill in the art. Such alternatives, variations, and modifications are intended to fall within the scope of the following appended claims.

What is claimed is:

1. A method for treating pain, comprising:
   implanting a pulse generator having a lead attached thereto;
   implanting the lead into a patient's lymphatic system by introducing the lead intravenously into a thoracic duct and thence to a selected location within a lymphatic vessel;
   disposing an electrode incorporated into the lead at a selected location within the lymphatic vessel so as to be near selected nervous tissue responsible for a patient's chronic pain; and,
   delivering electrical stimulation from the pulse generator to the electrode incorporated into the lead in a manner that reduces the patient's pain.

2. The method of claim 1 wherein the electrical stimulation is delivered in a form selected from a group including a DC pulse, a biphasic pulse, a multi-phasic pulse, and a pulse train at a selected frequency for a selected duration.

3. The method of claim 1 further comprising initiating delivery of the electrical stimulation by actuating a manually operated switch incorporated into the pulse generator.

4. The method of claim 3 wherein the switch is a tactilely actuated switch.

5. The method of claim 3 wherein the switch is a magnetically actuated switch.

6. The method of claim 1 further comprising initiating delivery of the electrical stimulation by transmitting a command to a telemetry transceiver incorporated into the pulse generator.

7. The method of claim 1 further comprising programming a controller incorporated into the pulse generator to deliver the electrical stimulation in accordance with a defined schedule.

8. The method of claim 1 further comprising delivering the electrical stimulation with a unipolar lead such that a voltage generated by the pulse generator is imposed between the electrode of a unipolar lead and a conductive housing of pulse generator.

9. The method of claim 1 further comprising delivering electrical stimulation with a bipolar lead such that a voltage generated by the pulse generator is imposed between two electrodes of the bipolar lead.

10. A method for treating pain due to edema, comprising:
- implanting a pulse generator having a lead attached thereto;
- implanting the lead into a patient's lymphatic system by introducing the lead intravenously into a thoracic duct and thence to a selected location within a lymphatic vessel;
- disposing an electrode incorporated into the lead at a selected location within the lymphatic vessel so as to be near selected areas of edema; and,
- delivering electrical stimulation from the pulse generator to the electrode incorporated into the lead to elicit smooth muscle fiber activation and lymphatic vessel contraction in a manner that reduces the edema.

\* \* \* \* \*